(12) United States Patent
Sugiyama

(10) Patent No.: US 6,177,670 B1
(45) Date of Patent: Jan. 23, 2001

(54) METHOD OF OBSERVING SECONDARY ION IMAGE BY FOCUSED ION BEAM

(75) Inventor: Yasuhiko Sugiyama, Chiba (JP)

(73) Assignee: Seiko Instruments Inc. (JP)

( * ) Notice: Under 35 U.S.C. 154(b), the term of this patent shall be extended for 0 days.

(21) Appl. No.: 09/235,667

(22) Filed: Jan. 22, 1999

(30) Foreign Application Priority Data

Jan. 23, 1998 (JP) .................................................. 10-011538

(51) Int. Cl.⁷ .................................................... H01J 29/58
(52) U.S. Cl. ................. 250/307; 250/492.2; 250/492.21; 250/397
(58) Field of Search .................................. 250/307, 309, 250/306, 492.2, 492.21, 397

(56) References Cited

U.S. PATENT DOCUMENTS

| 4,933,565 | * | 6/1990  | Yamaguchi et al. | 250/492.2 |
| 5,065,034 | * | 11/1991 | Kawanami et al.  | 250/505.1 |
| 5,739,528 | * | 4/1998  | Kato             | 250/251   |
| 5,824,598 | * | 10/1998 | Yamaguchi et al. | 438/676   |

* cited by examiner

Primary Examiner—Teresa M. Arroyo
Assistant Examiner—Nikita Wells
(74) Attorney, Agent, or Firm—Adams & Wilks

(57) ABSTRACT

A high-resolution secondary ion image is observed by first and second processing steps. In the first step, the focus of the ion optics is adjusted while observing a secondary electron image at an image refresh rate of a few or several seconds. In the second step, secondary ions are detected with a secondary charged-particle detector without readjusting the focus of the ion optics. A secondary ion image is observed at a scanning rate of tens to hundreds of seconds/frame. Thus, a focused high-resolution secondary ion image is derived.

3 Claims, 3 Drawing Sheets

METHOD OF OBSERVING SECONDARY ION IMAGE BY FOCUSED ION BEAM

BACKGROUND OF THE INVENTION

The present invention relates to a method of performing processing to form a cross section at a certain location on a semiconductor device, using a focused ion beam, for defect analysis or the like and of observing the cross section.

As LSIs (large-scale integrated circuits) and so on are fabricated with increasing device densities and in smaller size, techniques for processing and observing cross sections of the LSIs during development steps and fabrication steps with a focused ion beam device have been shown.

In particular, the position of a cross section to be processed is determined by the functions of a scanning ion microscope. Using the processed cross section as a plane, a rectangular hole is formed by maskless etching function. A desired cross-sectional portion is exposed, and then the sample is tilted to direct the cross-sectional portion in the direction of illumination of the ion beam. The processed cross section is observed again by the functions of the scanning ion microscope.

When the cross-sectional portion fabricated by the aforementioned method is observed by the functions of a scanning ion microscope, the ion current of the focused ion beam is set less than 5 pA to reduce the beam diameter. In this way, a high-resolution image is obtained. However, as the beam current decreases, the intensity of the secondary charged-particle signal also decreases, thus deteriorating the signal-to-noise ratio. Especially, the intensity of secondary ions is only approximately $1/10$ to $1/1000$ of the intensity of secondary electrons. Therefore, with scanning at an image refresh rate of a few or several seconds necessary for adjustment of the focus of the focused ion beam, the S/N is low. Image quality necessary for the work cannot be obtained. It has been difficult to finely adjust the voltage applied to the objective lens while watching the image of poor quality, to bring the focus of the focused ion beam onto the sample, and to obtain a high-resolution image of less than 10 nm. It is customary to slow the frame scanning rate as a method of improving the S/N. This method increases the time for which the secondary ion signal is accumulated to thereby improve the image quality. However, the image refresh rate is low. Therefore, skillfulness is necessary to adjust the focus of the focused ion beam while watching this image. It is not easy for everyone to make an adjustment.

SUMMARY OF THE INVENTION

The problem described above is solved by the present invention comprising first and second processing steps. In the first step, secondary electrons are detected by a secondary charged-particle detector. The focus of an ion optics is adjusted while observing a secondary electron image. In the second step, secondary ions are detected with the secondary charged-particle detector without readjusting the focus of the ion optics adjusted in the first step. A secondary ion image is observed. Thus, a focused high-resolution secondary ion image is obtained.

DETAILED DESCRIPTION OF THE INVENTION

Figure 1:
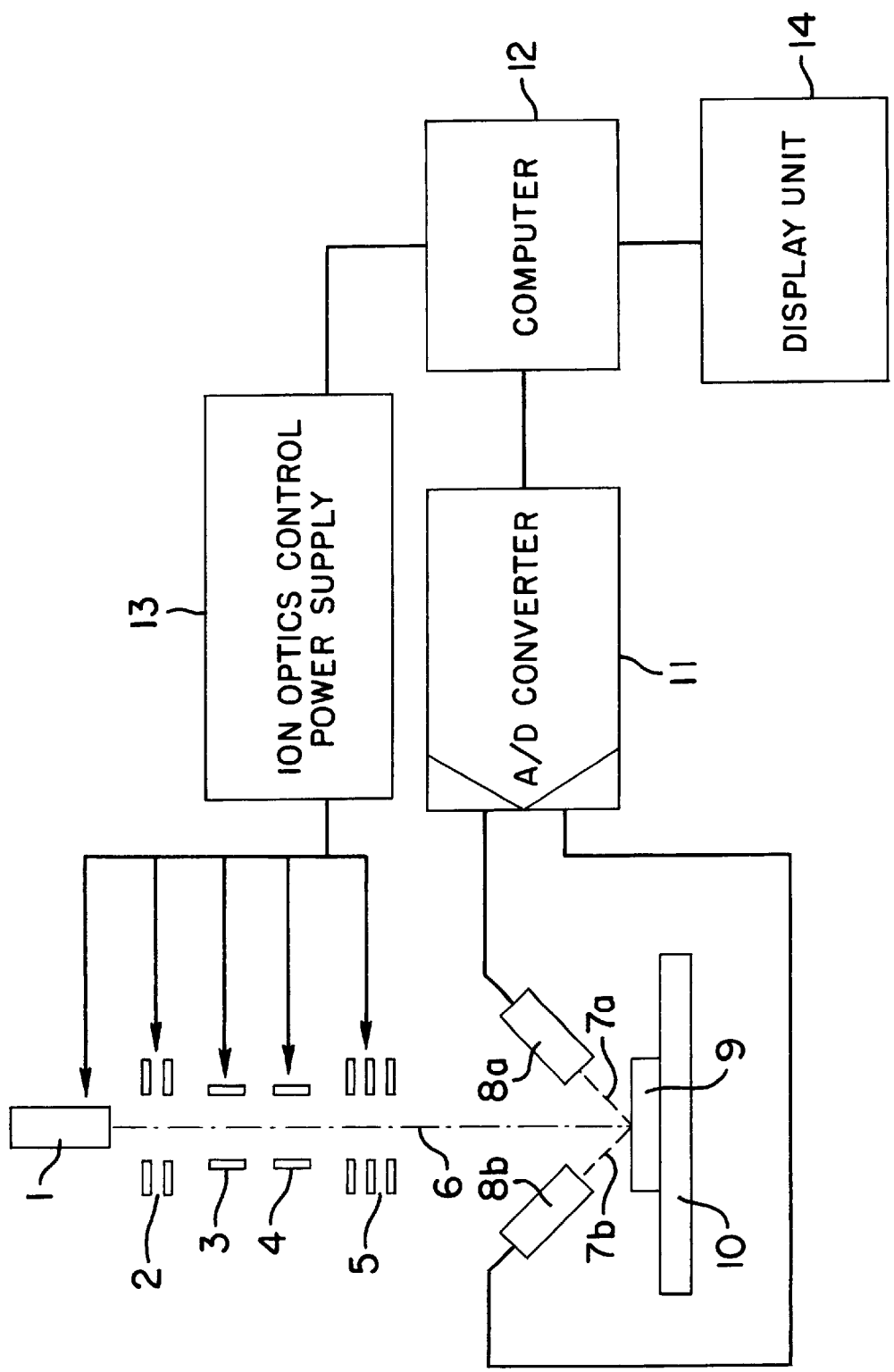
FIG. 1 is a block diagram of an instrument for carrying out the present invention.

The configuration of an instrument is described by referring to FIG. 1. As shown in FIG. 1, an example of instrument for embodying the present invention is fitted with a focused ion beam-generating portion comprising a liquid metal ion source 1, a condenser lens 2 for condensing an ion beam extracted from the liquid metal ion source 1, an objective lens 5, and a blanking electrode 3 for turning on and off the ion beam over a sample. A deflection electrode 4 for deflecting and scanning the focused ion beam is disposed on the axis of the focused ion beam 6. The instrument further includes a movable sample stage 10 on which a sample 9 illuminated with the focused ion beam 6 is placed, secondary charged-particle detectors 8a, 8b for detecting secondary charged particles 7a and 7b emitted by the illumination of the focused ion beam 6, a display unit 14 for displaying an image of a surface of the sample 9 according to the intensities of the secondary charged particles 7a and 7b detected by the secondary charged-particle detectors 8a, 8b, and so on.

The secondary charged-particle detectors 8a and 8b consist of the secondary electron detector 8a for detecting the secondary electrons 7a and the secondary ion detector 8b for detecting secondary ions 7b. The secondary charged-particle detectors 8a and 8b may be composed of one detector, and this may be switched between the secondary electron detector 8a and the secondary ion detector 8b with a switch.

Signals from the secondary charged-particle detectors 8a and 8b are applied to an A/D converter 11, where A/D conversion is performed. The signals of the secondary charged particles 7a and 7b converted into digital signals are arithmetically processed by a computer 12 to display an image on the display unit 14. Electric power to the liquid metal ion source 1, the condenser lens 2, the blanking electrode 3, the deflection electrode 4, and the objective lens 5 is supplied based on a signal from the computer 12 via an ion optics control power supply 13. It consists of the secondary electron detector 8a for detecting the secondary electrons 7a and the secondary ion detector 8b for detecting the secondary ions 7b.

Figure 2A:
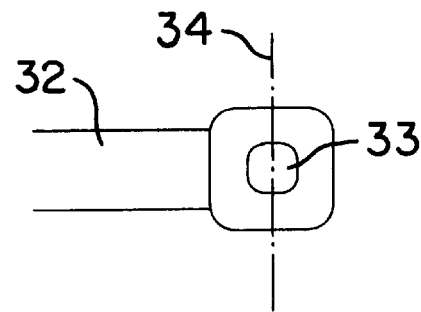
FIG. 2A–2C are plan views of a sample surface illustrating a cross section-micromachining method.

A method of processing and observing a cross section using the focused ion beam system is hereinafter described by referring to FIG. 2. An LSI was used as the sample 9 whose cross section was to be observed. As shown in FIG. 2A, a scanning ion microscope image including a contact hole 33 of the sample 9 of LSI to be observed is found.

Conductive interconnects 32 are observed near the contact hole 33. A scanning ion microscope image is obtained by directing the focused ion beam 6 to the surface of the sample 9 while scanning it and detecting the secondary electrons 7a or the secondary ions 7b that are secondary charged particles emanating from the surface of the sample 9. A position 34 where a cross section is to be formed is established from the image of FIG. 2A.

Figure 2B:
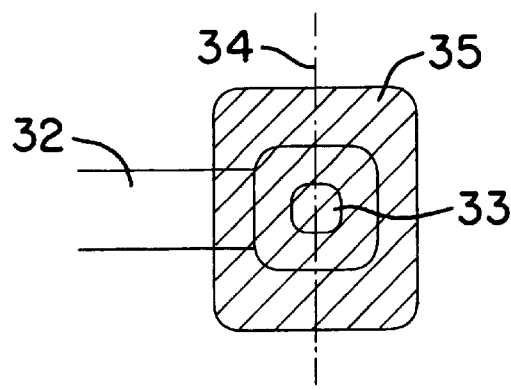

Then, as shown in FIG. 2B, a region 35 containing the contact hole 33 is coated with a film by an FIB-CVD method. In the FIB CVD method, a source gas is made to adsorb on the surface of the sample by a gas gun (not shown). The ion beam 6 accelerated at an energy of 20 to 30 KeV is scanned within the region 35 and illuminates it. In this way, a film is selectively formed only on the illuminated region 35. In the present embodiment, $W(CO)_6$ is used as the source gas, and a tungsten film is formed. Of course, the present invention can be practiced by using a different gas and forming other metal film. If this formation of the film is performed for a long time, the surface of the coated region of the sample is flattened. Conductive patterns are not easily discernible on the scanning ion microscope image. Consequently, where the formation of the film is completed before the planarization, the cross section is formed with greater ease.

Figure 2C:
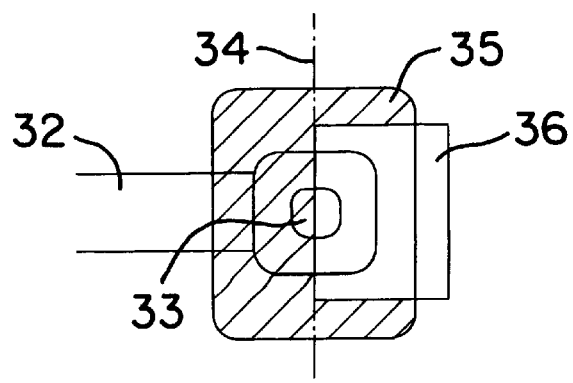
Figure 3:
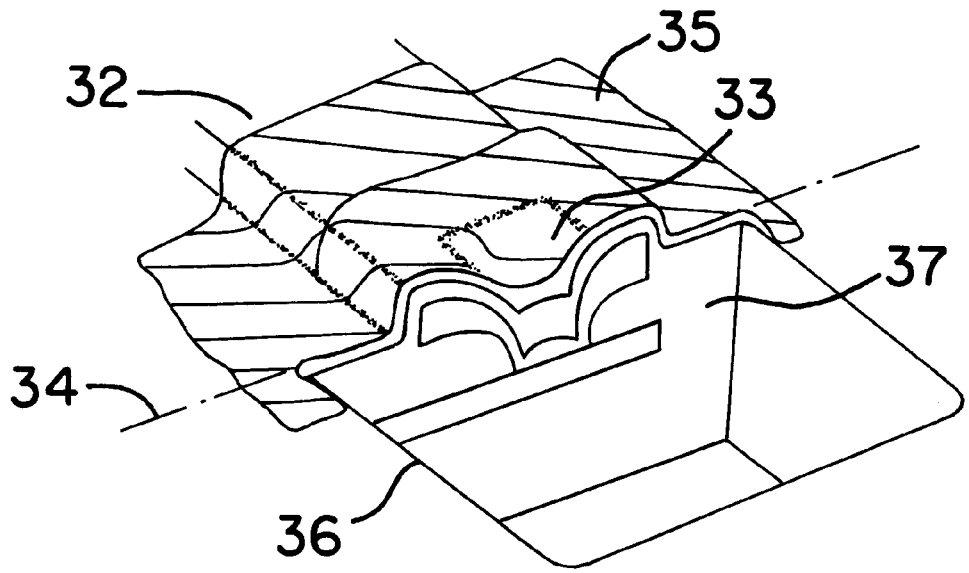
FIG. 3 is a perspective view of a cross section of a sample processed.
Figure 4:
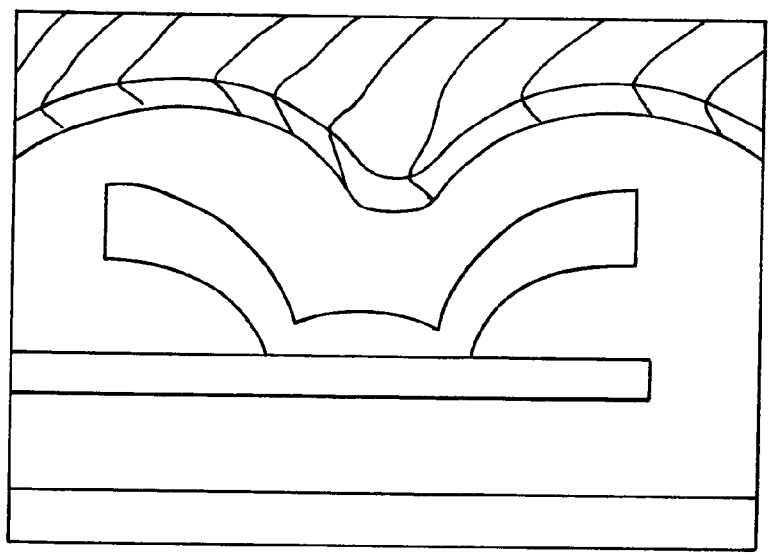
FIG. 4 is a diagram of a secondary electron image.

After the film formation, the focused ion beam 6 is directed to an etched region 36 to perform an etching operation, as shown in FIG. 2C. The etched region 36 is almost rectangular and has one side lying at the position 34 where the cross section is formed. Rough drilling is done at high current beams, such as 2 to 10 nA. Finished drilling is done by directing the beam to the position 34 of the cross section to be observed at moderate current beams, such as 30 pA to 2 nA. A perspective view of the cross section of the sample processed is shown in FIG. 3. In consequence, a sidewall cross section 37 is formed, as shown in FIG. 4.

Then, the sample stage 10 is tilted to expose the processed cross section 37 of the sample 9 in the direction of illumination of the ion beam. This cross section 37 is observed with a scanning ion microscope at a relatively low current beam (e.g., less than 1 pA).

Where an abnormal portion such as a foreign material whose cross section is to be observed is small, the cross section may be formed without coating. Also, in this case, more accurate cross-sectional shape can be obtained by performing operations described above.

To obtain a high-resolution image when the cross section 37 prepared by the method described above is observed by the functions of the scanning ion microscope, the current of the focused ion beam 6 is set less than 5 pA, thus narrowing the beam diameter. As a first processing step, the focus of the ion optics is adjusted while observing the secondary electron image at an image refresh rate of a few or several seconds. The image may be either a frame-accumulated image or a dot-accumulated image.

Where sufficient image quality is derived, the image refresh rate can be less than 1 second. The secondary electron detector 8a is used to detect the secondary electrons 7a. As a result, a secondary electron image as shown in FIG. 4 is obtained. The voltage applied to the objective lens 5 is finely adjusted while watching this image. The focus is brought to the sample 9. A high-resolution secondary electron image is obtained. More secondary electrons are produced than secondary ions. Therefore, if the image refresh rate is a few or several seconds, the image is obtained with relatively high signal-to-noise ratio. It is easy to adjust the focus.

As the second processing step, the secondary ion detector 8b is used to detect the secondary ions 7a. At this time, the focus of the objective lens 5 has been already adjusted by the first processing step and thus does not need readjustment. However, the detected ions are switched between the secondary electrons 7a and the secondary ions 7b and so the polarity of the pull-in voltage applied to the charged-particle detectors 8a and 8b varies. Therefore, the field of view varies between the secondary ion image and the secondary electron image. In the present embodiment, a DC voltage is superimposed on the deflection electrode 4. The position of the focused ion beam 6 is deflected. The size is adjusted. Thus, the field of view is adjusted, and an image is obtained.

Subsequently, secondary ion images are accepted at a scanning rate of tens to hundreds of seconds/frame. Consequently, a secondary ion image with good S/N at an image resolution of less than 10 nm is obtained.

In the present invention, when a secondary ion image of small signal intensity is observed, the ion optics is adjusted while observing a secondary electron image producing a relatively large amount of signal. Then, a secondary ion image is observed. In this way, a focused, secondary ion image can be easily obtained.

What is claimed is:

1. A method of observing a secondary ion image by a focused ion beam, comprising the steps of:

adjusting the focus of a ion optics while detecting secondary electrons with a secondary charged-particle detector and observing a secondary electron image, using a focused ion beam (FIB) system, said FIB system comprising:

a focused ion beam-generating portion comprising a liquid metal ion source, the ion optics for focusing an ion beam extracted from said ion source, and a blanking electrode for turning on and of f said ion beam over a sample;

a deflection electrode for deflecting and scanning said focused ion beam;

a movable sample stage on which a specimen illuminated with said focused ion beam is placed; and a secondary charged-particle detector for detecting secondary charged particles emitted by the illumination of said focused ion beam; and detecting the secondary ions with the secondary charged-particle detector without readjusting the focus of the ion optics adjusted by the first-mentioned step and observing a secondary ion image.

2. A method of observing a secondary ion image by a focused ion beam as set forth in claim 1, wherein said secondary charged-particle detector consists of a detector used to detect only secondary ions and another detector used to detect only secondary electrons.

3. A method of observing a secondary ion image by a focused ion beam as set forth in claim 1, wherein said secondary charged-particle detector is a secondary charged-particle detector for detecting secondary electrons while setting a pull-in voltage to positive polarity and for detecting secondary ions while setting the pull-in voltage to negative polarity and is provided with a compensating means for compensating for variations in the position hit by said focused ion beam by switching the polarity of said pull-in voltage, said method comprising the steps of:

adjusting the focus of the ion optics while detecting secondary electrons with the secondary charged-particle detector and observing a secondary electron image; and detecting secondary ions with the secondary charged-particle detector without readjusting the focus of the ion optics adjusted by the first-mentioned step, making an adjustment such that the field of view of the secondary electron image and the field of view of the secondary ion image are brought into the same position by the compensating means for compensating for variations in the position hit by the focused ion beam, and observing the secondary ion image.

* * * * *